United States Patent [19]

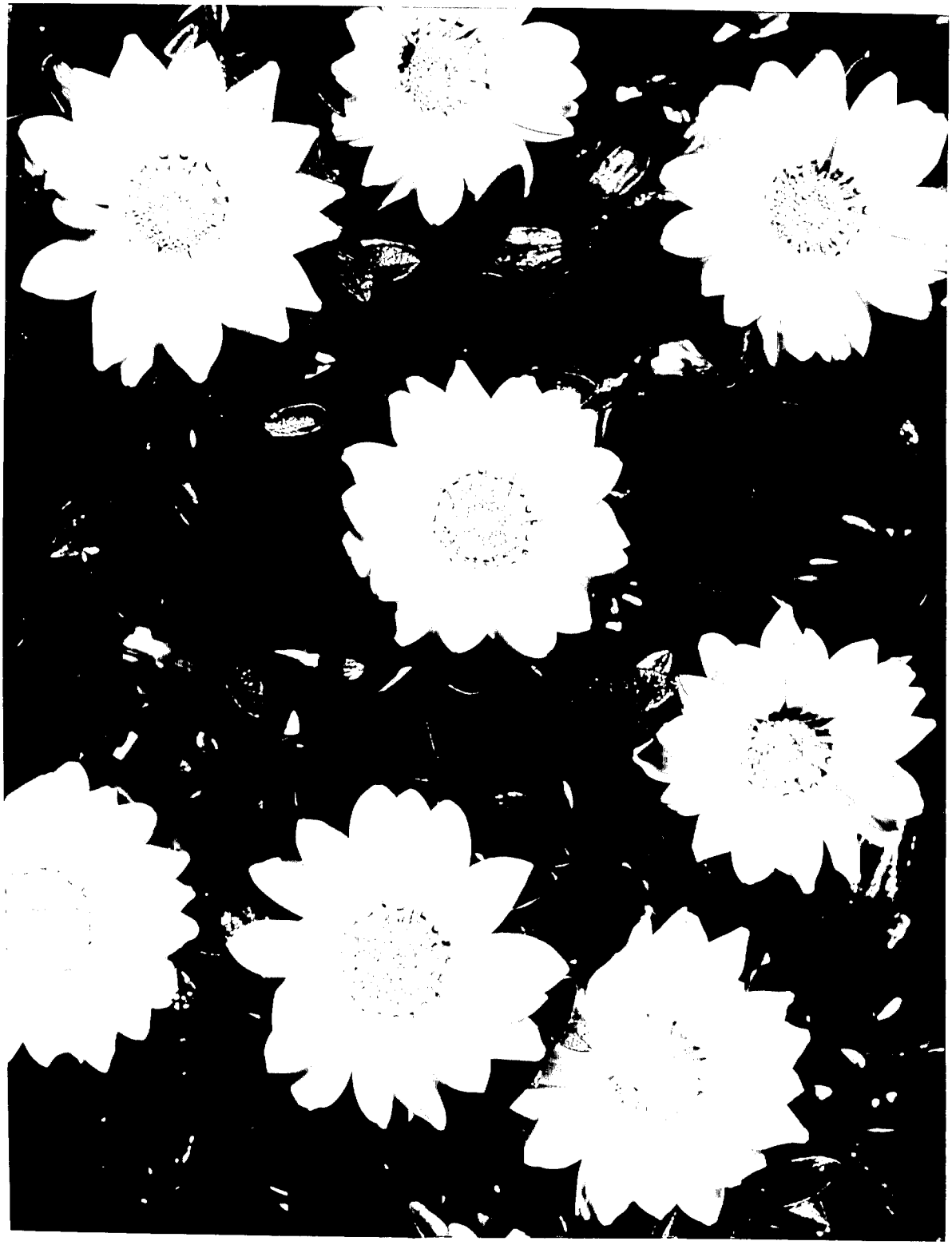

Ono

[11] Patent Number: Plant 5,796

[45] Date of Patent: Nov. 4, 1986

[54] GAZANIA PLANT CALLED MITSUWA ORANGE

[75] Inventor: Toshiaki Ono, Chatsworth, Calif.

[73] Assignee: Mitsuwa Nursery, Inc., Moorpark, Calif.

[21] Appl. No.: 746,525

[22] Filed: Jun. 19, 1985

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Roylance, Abrams, Berdo & Goodman

[57] ABSTRACT

A Gazania named Mitsuwa Orange having bright orange flowers which is much easier to propagate as compared to other orange trailing Gazanias, and which is very consistent as to the bright orange color in successive propagations. The foilage is noteworthy for having two characteristics not heretofore found together in any other Gazania; dark green leaves and a full trailing habit.

1 Drawing Figure

BACKGROUND OF THE INVENTION

The present invention relates to a new and distinctive cultivar of Gazania plant botanically known as *Gazania rigens Mitsuwa Yellow,* and referred to commercially by the cultivar name "Mitsuwa Orange".

"*Rigens*" is the Latin botanical name given by the County Arboretum of Los Angeles, Calif. to the first of the Mitsuwa Gazanias called Mitsuwa Yellow, (registered trademark). Mitsuwa Yellow is commercially well known. Mitsuwa Orange is virtually identical in appearance and growing habits to Mitsuwa Yellow, except for the substantial difference in the color of the flowers.

BRIEF DESCRIPTION OF THE INVENTION

Gazanias, in general, are a genus of herbs of the aster family which are characterized by large, showy, orange and yellow blossoms and which prefer bright sunshine. They are native to South Africa but are now widely cultivated and are commercially important. Gazanias were named after Theodorus Gaza, a medieval Greek scholar of Italy.

DESCRIPTION OF THE DRAWING

The accompanying color photograph, forming a part of this disclosure, was taken in March of 1985 in Moorpark, Calif., and shows Mitsuwa Orange growing in a bed; the view being more or less looking straight down onto the plant. The photograph shows the colors of all parts of Mitsuwa Orange as true as is reasonably possible in this type of color photograph.

DETAILED DESCRIPTION

Mitsuwa Orange is a spontaneous sport or mutant discovered by Mr. Toshiaki Ono in the nursery of Mitsuwa Nursery, Inc. of Moorpark, Calif.

Asexual reproduction, starting by propagating cuttings from the originally discovered sport, has reproduced the unique features of this new plant through successive propagations. Crown cuttings (a major stem with several leaves) were used for this propagation. Mitsuwa Orange is distinguished from its parent and from all other commercial gazanias in general by several characteristics.

The color of the flowers of Mitsuwa Orange is very consistant. This of course makes it highly desirable to consumers and thus commercially valuable. With virtually all other commercially available varieties of gazanias there is at least some tendency to produce sports which are undesirable in that such sports display a substantial variance from true in shape, size and color of the flowers.

The Mitsuwa Orange plant and foilage has a double thrust improvement over the closest known existing variety of orange gazania. That prior known plant is, botanically, *Gazania uniflora leucoleana,* and is known commonly as orange trailing Gazania.

However, Mitsuwa Orange, as compared to this prior known plant, has dark green leaves and has a full trailing (spreading) habit. The prior plant has silver grey colored leaves, and has only a semi-trailing habit. Further, the leaves of Mitsuwa Orange are not only this richer dark green color but are also relatively wider.

There are other known Gazanias that have dark green leaves, but these do not have a full trailing habit. There are other known Gazanias that have a full trailing habit but do not have dark green leaves. Mitsuwa Orange is the only known Gazania to have both these desirable characteristics of dark green leaves and a full trailing habit.

Mitsuwa Orange, in the climate of southern California, in common with most other Gazanias, blooms nearly all year long.

Mitsuwa Orange is much easier to propagate than the other commercial orange trailing Gazania, *Gazania uniflora leucoleana.* More specifically, the time needed to produce a root system for Mitsuwa Orange is about 40% less than the time needed to produce a root system for *Gazania uniflora leucoleana.*

Color references herein, except where the ordinary dictionary meaning is clear from the context, are to the Royal Horticultural Colour Chart. The following characterizations were made by the discoverer and other personnel of Mitsuwa Nursery, Inc., based on the flowers shown in the photograph herein.

Flower, petal upside, Yellow Orange 21A
Flower, petal downside, Yellow Orange 14D
Leaves, upside, Green 137A
Leaves, downside, White 155D As shown in the photograph, Mitsuwa Orange also features a delicate ring of small black and white spots on the petals which further distinguishes Mitsuwa Orange from its Mitsuwa Yellow parent.

Mitsuwa Orange is a fine ground cover. In the southern California climate it has been found to be commercially valuable as a relatively inexpensive and efficient substitute for certain annual flowering plants. Mitsuwa Orange has been found to bloom more heavily in summer than its parent Mitsuwa Yellow.

The buds display the characteristic roughly acorn shape common to other Gazanias.

I claim:

1. A new and distinct cultivar of Gazania named Mitsuwa Orange, as described and illustrated, and particularly characterized by its bright orange flowers and its dark green foilage having a full trailing habit.

* * * * *